(12) United States Patent
Shaffer et al.

(10) Patent No.: US 12,226,510 B2
(45) Date of Patent: *Feb. 18, 2025

(54) SKIN TREATMENT METHODS AND COMPOSITIONS WITH RETINOID AND DELIVERY SYSTEMS THEREOF

(71) Applicant: Topix Pharmaceuticals, Inc., North Amityville, NY (US)

(72) Inventors: Burt R. Shaffer, Lloyd Harbor, NY (US); Steven M. Hernandez, Blue Point, NY (US)

(73) Assignee: Topix Pharmaceuticals, Inc., North Amityville, NY (US)

( * ) Notice: Subject to any disclaimer, the term of this patent is extended or adjusted under 35 U.S.C. 154(b) by 113 days.

This patent is subject to a terminal disclaimer.

(21) Appl. No.: 17/680,816

(22) Filed: Feb. 25, 2022

(65) Prior Publication Data

US 2022/0183951 A1 Jun. 16, 2022

Related U.S. Application Data

(63) Continuation of application No. 15/907,047, filed on Feb. 27, 2018, now Pat. No. 11,266,588.

(60) Provisional application No. 62/464,823, filed on Feb. 28, 2017.

(51) Int. Cl.

| | | |
|---|---|---|
| *A61K 8/67* | (2006.01) |
| *A61K 8/34* | (2006.01) |
| *A61K 8/49* | (2006.01) |
| *A61K 8/58* | (2006.01) |
| *A61K 8/60* | (2006.01) |
| *A61K 8/73* | (2006.01) |
| *A61K 8/891* | (2006.01) |
| *A61K 8/894* | (2006.01) |
| *A61K 9/00* | (2006.01) |
| *A61K 31/07* | (2006.01) |
| *A61K 36/82* | (2006.01) |
| *A61K 47/16* | (2006.01) |
| *A61K 47/34* | (2017.01) |
| *A61P 17/02* | (2006.01) |
| *A61P 17/06* | (2006.01) |
| *A61Q 19/00* | (2006.01) |
| *A61Q 19/02* | (2006.01) |
| *A61Q 19/08* | (2006.01) |

(52) U.S. Cl.
CPC ............. *A61K 8/671* (2013.01); *A61K 8/347* (2013.01); *A61K 8/4953* (2013.01); *A61K 8/585* (2013.01); *A61K 8/60* (2013.01); *A61K 8/735* (2013.01); *A61K 8/891* (2013.01); *A61K 8/894* (2013.01); *A61K 9/0014* (2013.01); *A61K 31/07* (2013.01); *A61K 36/82* (2013.01); *A61K 47/16* (2013.01); *A61K 47/34* (2013.01); *A61P 17/02* (2018.01); *A61P 17/06* (2018.01); *A61Q 19/00* (2013.01); *A61Q 19/007* (2013.01); *A61Q 19/08* (2013.01); *A61K 2800/28* (2013.01); *A61Q 19/02* (2013.01)

(58) Field of Classification Search
CPC ...... A61K 8/4953; A61K 8/671; A61K 8/735; A61K 8/89–899; A61Q 19/007; A61Q 19/08; A61P 17/00–18
See application file for complete search history.

(56) References Cited

U.S. PATENT DOCUMENTS

| | | |
|---|---|---|
| 5,605,929 A | 2/1997 | Liao et al. |
| 5,780,676 A | 7/1998 | Boehm et al. |
| 8,900,607 B1 | 12/2014 | Harrison et al. |
| 8,980,344 B2 | 3/2015 | Gross |
| 9,155,915 B2 | 10/2015 | Kunin |
| 2003/0049212 A1 | 3/2003 | Robinson et al. |
| 2005/0106110 A1 | 5/2005 | Liu |
| 2006/0263398 A1 | 11/2006 | Kalil |
| 2007/0154419 A1 | 7/2007 | Hattendorf et al. |
| 2008/0199421 A1 | 8/2008 | Lorant |
| 2009/0017147 A1 | 1/2009 | Lintner et al. |
| 2009/0068132 A1 | 3/2009 | Bratescu et al. |
| 2010/0080768 A1 | 4/2010 | McGraw et al. |
| 2010/0202986 A1 | 8/2010 | Raul et al. |
| 2013/0243835 A1 | 9/2013 | Tanner et al. |
| 2014/0161855 A1 | 6/2014 | Doucet et al. |
| 2015/0359893 A1 | 12/2015 | Zecchino et al. |

FOREIGN PATENT DOCUMENTS

| | | |
|---|---|---|
| CN | 1190888 A | 8/1998 |
| CN | 104185470 A | 12/2014 |
| DE | 10133203 A1 | 1/2003 |
| EP | 1837008 A2 | 9/2007 |

(Continued)

OTHER PUBLICATIONS

"Retinol 50C", Technical Information Data Sheet, BASF Personal Care Ingredients, Apr. 3, 2010, 10 pages, http://dewolfchem.com/wp-content/uploads/2013/08/Retinol-TDS2.pdf.
"Poetry in Lotion Intensive Retinol 1.0", Mintel, Mar. 12, 2009, 6 pages, http://www.gnpd.com.
Energising Moisturising Cream SPF 20 PA++, Mintel, Oct. 19, 2016, 4 pages, http://www.gnpd.com.
"Hydrablue Primer", Mintel, Feb. 29, 2016, 6 pages, http://www.gnpd.com.

(Continued)

Primary Examiner — Leigh C Maier
(74) Attorney, Agent, or Firm — Lowenstein Sandler LLP

(57) ABSTRACT

Disclosed are stable, non-irritating, retinoid containing formulations and delivery systems for topical application to the skin. The disclosed topical formulations and delivery systems provide controlled release of the retinoid to the skin for the treatment of amenable skin conditions as well as for improvement of aesthetic skin properties. Also provided are methods for the formulation, manufacture and use of the disclosed retinoid containing formulations and delivery systems.

24 Claims, No Drawings

(56) References Cited

FOREIGN PATENT DOCUMENTS

| FR | 2942962 A1 | 9/2010 | |
|---|---|---|---|
| KR | 20040067710 A | 7/2004 | |
| WO | 0203930 A2 | 1/2002 | |
| WO | WO-2013142472 A2 * | 9/2013 | ............... A61K 8/06 |
| WO | 2016139471 A1 | 9/2016 | |

OTHER PUBLICATIONS

Intensive Wrinkle Smoothing Cream, Mintel, Jul. 17, 2015, 6 pages, http://www.gnpd.com.

"Tretinol 0.5% Facial Serum", Mentel, Nov. 21, 2011, 5 pages, http://www.gnpd.com.

Extended European Search Report for European Patent Application No. 18761606.5, dated Nov. 30, 2020, 14 pages.

Fiume, M. et al "Safety assessment of propylene glycol . . . " Int. J. Toxicol., vol. 31, suppl. 2, pp. 245S-260S. (Year: 2012).

Rendon, M. et al "Evidence and considerations in the application of chemical peels" J. Clin. Aesthet. Dermatol., vol. 3, No. 7, pp. 32-43. Year: 2010).

International Preliminary Report on Patentability issued for for corresponding corresponding International International Patent Patent Application Application No. No. PCT/US2018/020010, mailed on Sep. 12, 2019.

Aburjai, T. et al "Plants Plants used in cosmetics" Phytother. Res., vol. 17, pp. 987-1000. (Year: Year: 2003).

Personal care products from Dow Coming(R), https://www.univar.com/~/media/PDFs/US%20Corp%20Region%20PDFs/PC/Dow%20Coming%20Personal%20Care%20Products%20from%20Jnivar.ashx, retrieved from internet Jan. 17, 2019 (Year: 2012).

International Search Report with Written Opinion, mailed Jun. 14, 2018, for corresponding international application PCT/US2018/020010.

BASF Tech Bulletin; Retinol; BASF SE—Care Chemicals Division—Personal Care Ingredients—67056 Ludwigshafen—www.personal-care.basf.com; Apr. 2010.

DSM Retinol Product Data Sheet; Retinol GS 50; Oct. 14, 2013.

\* cited by examiner

SKIN TREATMENT METHODS AND COMPOSITIONS WITH RETINOID AND DELIVERY SYSTEMS THEREOF

CROSS-REFERENCE TO EARLIER APPLICATIONS

The present application is a Continuation Application of U.S. application Ser. No. 15/907,047 filed on Feb. 27, 2018, which claims priority under 35 U.S.C. § 119(e) to U.S. Provisional Patent Application Ser. No. 62/464,823, filed Feb. 28, 2017, the entire contents of which are incorporated herein by reference.

FIELD

The present invention relates to the field of dermatological compositions and methods for skin treatments having at least one retinoid and delivery systems thereof, including dermatological compositions and methods having retinol and delivery systems thereof, for topical application to the skin, as well as to methods for their formulation, manufacture and use thereof.

BACKGROUND

Retinoids are useful in the treatment of various and diverse dermatological conditions, including inflammatory disorders, conditions characterized by increased cell turnover such as psoriasis, photoaging, age spots, skin wrinkles, acne, and skin cancers.

However, retinoids, particularly retinol, are unstable and easily oxidized in the presence of air as well as in the presence of ingredients commonly used in cosmetic formulations. This can be a serious issue when applied as a thin layer to a relatively large surface area of the skin.

Retinol can also be very difficult to release from prior art delivery systems, resulting in greatly reduced efficiency of delivery even with relatively high concentrations of retinol in the formulation. Accordingly, although a first formulation may include a higher concentration of a retinoid or retinol than a second formulation, the latter may be more efficient with respect to delivery of the retinoid or retinol if its formulation provides enhanced release of the active agent, retinoid or retinol.

Retinol can also be irritating to the skin, discouraging continued application by those in need of treatment with retinol-containing formulations, and thereby reducing if not eliminating efficacy of the treatment. Typically, retinol formulations having 4% to 6% of the active agent are used for dermatological applications, such as chemical skin peeling. Such formulations generally must be applied by professional staff or under medical supervision during skin treatments and are more prone to the aforementioned skin irritating affects.

Available retinoid and retinol formulations include solvent-based systems, ointments, water-based formulations, emulsions, gels and lotions, all of which vary in their stability and their efficiency. As such, retinoid and retinol formulations are underutilized for pre-treatment, e.g., chemical peeling, or other skin care procedures, due to the propensity to irritation.

Accordingly, there is a need in the art for topical formulations and delivery systems that can provide retinoids to the skin of those in need thereof to alleviate and ameliorate one or more of the exemplary conditions noted above, as well as others that are recognized in the field of dermatological and cosmetic skincare procedures.

The present disclosure provides new, improved formulations and delivery systems for retinol and other members of the retinoid family that maintain product stability, that exhibit low irritancy, and yet provide increased efficiency of release and delivery of the active agent retinol or another member of the retinoid family. Such formulations and delivery systems disclosed herein include use as chemical peels, and as pre-treatment agents for dermatological and cosmetic skincare procedures.

SUMMARY

The present disclosure provides a retinoid delivery system, and more particularly, a retinol delivery system. The delivery system exhibits product stability, low irritancy and improved efficiency of delivery of the formulated retinoid. In particular, the present disclosure provides a delivery system that exhibits product stability, low irritancy and improved efficiency of delivery of the formulated retinol.

The present disclosure provides formulations comprising one or more retinoids, including retinol, that are useful in the disclosed delivery system. The disclosed formulations provide retinoid stability, low irritancy, and efficient release of the active agent retinoid/retinol, when applied to the skin. In one aspect of this disclosure the skin is human skin. In other aspects of the present disclosure, the skin is that of a companion animal, a domestic animal, or a commercially useful animal.

The disclosed delivery system comprises one or more polymers acting as, inter alia, solvents. In one aspect of this embodiment, the polymer is a silicone elastomer. In another aspect, the silicone elastomer exhibits a degree of polarity, provided, for example, by ethoxylation or propoxylation or by modification with other materials that provide a degree of polarity to the silicone elastomer. In one specific aspect of this embodiment, the polymer is a PEG-12 dimethicone/PPG-20 copolymer.

The disclosed delivery system also comprises one or more solubilizing agents, rheology modifiers, emulsifiers and/or dispersion aids. In one aspect of this embodiment, the solubilizing agent/emulsifier is a non-ionic solubilizing agent/emulsifier. In one specific aspect of this embodiment, the solubilizing agent/emulsifier is caprylyl methicone. In another specific aspect of this embodiment, the solubilizing agent/emulsifier is PEG/PPG-18/18 dimethicone. In still another specific aspect of this embodiment, the solubilizing agent/emulsifier is polysorbate 20. In another specific aspect of this embodiment, the solubilizing agent/emulsifier is mixture of two or more materials including, but not limited to, a mixture of two or more of caprylyl methicone, PEG/PPG-18/18 dimethicone, and polysorbate 20.

The disclosed delivery system also comprises at least one retinoid source. In one aspect of this embodiment, the retinoid may be retinol, retinaldehyde, an ester of retinol, including, e.g., palmitate and stearate esters of retinol, retinoic acid, or a synthetic retinoid such as adapalene, bexarotene, tazarotene or a combination of two or more thereof. In one aspect of this embodiment, the retinoid is retinol. In another aspect, the retinoid is all trans-retinol.

The disclosed delivery system also comprises at least one liquid carrier/diluent. In one aspect of this embodiment the liquid carrier/diluent is a silicone. In another aspect of this embodiment, the silicone is mixed with or contains a volatile component. In one specific aspect the carrier/diluent is dimethicone; in another specific aspect the carrier/diluent is cyclomethicone, and in another it is caprylyl methicone. In a further aspect, the carrier/diluent is a mixture comprising dimethicone and cyclomethicone, and in another the carrier/diluent is a mixture comprising dimethicone, cyclomethicone, and caprylyl methicone, or another volatile or light and/or smooth feeling silicone.

The disclosed delivery system may also comprise one or more antioxidants. In one aspect of this embodiment, the antioxidant is a polyphenol. In a more specific aspect of this embodiment, the antioxidant comprises a polyphenol isolate of *Camellia sinensis*. In a further aspect, the antioxidant comprises 90% or 95% polyphenol isolate of *Camellia sinensis*.

The disclosed delivery source may also comprise a xanthine related compound, polymeric derivative thereof, or mixture of xanthine-related materials that can function as antioxidants or stimulators of antioxidant activity. In one specific aspect, the xanthine-related compound is caffeine.

The disclosed delivery system may also comprise one or more moisturizers and/or humectants. In one aspect of this embodiment, the moisturizer and/or humectant is sodium hyaluronate.

The disclosed delivery system may also comprise one or more emollients. In one aspect of this embodiment the emollient is an ester or oil. In various aspects of this embodiment, the emollient can include one or more of the following shea butter, cocoa butter, mineral oil, lanolin, petrolatum, paraffin, beeswax, squalene, cetyl alcohol, olive oil, triethylhexanoin, coconut oil, jojoba oil, sesame oil, almond oil, or other plant oils, and combinations of two or more thereof.

As discussed in further detail below, aspects of the present disclosure include a topical formulation comprising a silicone elastomer, a solubilizing agent, a retinoid, and a silicone based liquid carrier. The formulation may further comprise one or more of an antioxidant, a xanthine, a moisturizer, and an emollient.

In certain aspects of the present disclosure, the retinoid is all trans-retinol. In other aspects, the silicone elastomer is PEG-12/PPG-20 crosspolymer. In further aspects, the solubilizing agent is at least one of caprylyl methicone, PEG/PPG-18/18 dimethicone, polysorbate 20, and mixtures thereof. In yet further aspects, the silicone based liquid carrier is at least one of dimethicone, cyclomethicone, and mixtures thereof. In yet further aspects of the present disclosure, the antioxidant is *Camellia sinensis* polyphenols, the xanthine is caffeine, the moisturizer is sodium hyaluronate.

In certain aspects disclosed herein, retinoid formulations comprise (% w/w) 5%-85% caprylyl methicone; 5%-20% PEG-12 dimethicone/PPG-20 crosspolymer; 0.1%-40% dimethicone; 0.1%-10% caffeine; 0.01%-40% cyclomethicone; 0.1%-10% PEG/PPG-18/18 dimethicone; 0.1%-2.5% *Camellia sinensis* green tea polyphenols; 0.001%-60% retinol; 0.001%-5% sodium hyaluronate; 0.01%-25% polysorbate 20. The *Camellia sinensis* green tea polyphenols may be a 90%-100% pure preparation and the retinol all trans-retinol. In other aspects of the present disclosure, the all trans-retinol is at least 90% pure all trans-retinol, either neat or in a vehicle. In yet other aspects, the all trans-retinol is at least 95% pure all trans-retinol, either neat or in a vehicle.

Further aspects of the present disclosure include retinoid formulations comprising (% w/w) 40%-70% caprylyl methicone; 10%-20% PEG-12 dimethicone/PPG-20 crosspolymer; 10%-20% dimethicone; 1%-5% caffeine; 0.1%-3% cyclomethicone; 1.0%-2.5% PEG/PPG-18/18 dimethicone; 1.0%-5% *Camellia sinensis* green tea polyphenols; 0.1%-1.0% retinol; 0.01%-1.0% sodium hyaluronate; 0.1%-5% polysorbate 20.

Aspects of the present disclosure are directed to a method for therapeutic treatment of a dermatological condition. The method includes topically applying to an affected area a therapeutically effective amount of a formulation comprising a silicone elastomer, a solubilizing agent, a retinoid, and a silicone based liquid carrier. The method may further include exfoliating affected skin. The affected area may be one or more of human skin, scalp, hair, nails.

In aspects of the disclosed method for therapeutic treatment, the retinoid is retinol and may be all trans-retinol. In other aspects herein, the method includes topically applying the formulation as pre-treatment for application of a topical agent for treatment of the dermatological condition. The pre-treatment may include chemical peeling of the affected area. In other aspects herein, applying the formulation includes peeling the skin by applying the formulation and exfoliating affected skin comprises chemical peeling of the affected skin.

DETAILED DESCRIPTION

The present disclosure provides retinoid formulations, delivery systems and methods of use thereof for alleviation or amelioration of dermatological conditions amenable to treatment with retinoids, including retinol. The present disclosure further provides retinoid formulations, delivery systems and methods of use thereof for the treatment of skin, e.g., as pre-treatment agents and as chemical peels, that are used for skin treatment. Amenable conditions include, without limitation, inflammatory disorders of the skin and skin conditions characterized by increased cell turnover including psoriasis, photoaging, weather-beaten appearance, yellowing, loss of elasticity, loss of collagen rich appearance and/or youthfulness, redness, dryness, age spots, skin wrinkles, acne, rosacea, ichthyosis, as well as skin cancers. The disclosed retinoid formulations and delivery systems are also useful for improvement in one or more aesthetic criteria, including, but not limited to, a perceived improvement in apparent skin age, skin tone, weather-beaten appearance, yellowing, loss of elasticity, redness, dryness, age spots, skin wrinkles, skin smoothness, brightness, radiance, as well as skin pores becoming less noticeable.

As used herein, the terms "treatment" or "treating" with respect to a skin condition generally mean "having positive effect on a skin condition" and encompass reduction, amelioration, and/or alleviation of at least one symptom of a skin condition, a reduction, amelioration, and/or alleviation in the severity of the skin conditions, delay, prevention, or inhibition of the progression of the skin condition, or a perceived improvement or benefit as a result of the treatment. Treatment, as used herein, therefore does not require total curing of the condition. A formulation or delivery system of the present disclosure that is useful for treatment of a skin condition, or a delivery system or a method of treating a skin condition, need only reduce the severity of a skin condition, reduce the severity of symptoms associated therewith, provide improvement to a patient's quality of life, or delay, prevent, inhibit the onset of one or more symptoms of a skin condition, or provide a perceived benefit. As used herein, these terms also encompass aesthetic improvements to the skin upon application of the disclosed retinoid containing formulations and delivery systems. For example, the present disclosure contemplates the treatment of skin with chemical peeling, and as pre-treatments, used for skin treatment.

As used herein, the terms "application," "apply," and "applying" with respect to a disclosed topical retinoid formulation or delivery system, or method of using a disclosed topical retinoid formulation or delivery system, refer to any manner of administering a topical retinoid formulation or delivery system to the skin of a patient which, in medical or cosmetology practice, delivers the retinoid formulation or delivery system to the patient's skin surface. Smearing, rubbing, spreading, spraying a disclosed topical retinoid formulation or delivery system, with or without the aid of suitable devices, on a patient's skin are all included within the scope of the term "application," as used herein. The terms "topical" or "topically" with respect to administration or application of a disclosed retinoid formulation or delivery system refer to epicuatenous administration or application, or administration onto skin.

As used herein, the phrase "effective amount" refers to an amount of a retinoid formulation or delivery system, or component thereof, effective to treat a skin condition as noted above, including a range of effects, from a detectable local improvement in an area of topical application to substantial relief of symptoms to an improvement in one or more aesthetic criteria, including, but not limited to, a perceived improvement in apparent skin age, radiation damage, sun or UV damage, skin tone, weather-beaten appearance, yellowing, loss of elasticity, redness, dryness, age spots, skin wrinkles, skin smoothness, brightness, radiance, as well as skin pores becoming less noticeable. The effective amount will vary with the particular condition or conditions being treated, the severity of the condition, the duration of the treatment, the specific components of the composition being used, and other factors. More specifically, the disclosed compositions and formulations provide a method for stabilizing and delivering retinoids, including retinol in an efficacious manner to the skin. The disclosed compositions, formulations, delivery system, and methods of use thereof reduce, minimize, or eliminate normally-observed retinoid-induced dermatoses including, inter alia, itching, severe skin flaking, breakdown of the skin barrier, discomfort, extreme dryness, cracking of the skin and sensitization. The disclosed compositions, formulations, delivery system, and methods of use thereof also provide aesthetic improvements in the skin, including but not limited to skin that appears younger, skin exhibiting a more even tone, skin in which the pores are less noticeable, and skin that is judged by the user to be smoother, and/or to be improved with respect to its weather-beaten or aged appearance, yellowing, loss of elasticity, redness, dryness, age spots, and/or skin wrinkles.

The delivery system disclosed herein not only maintains product stability, including stability of the formulated retinoid as well as the antioxidant, but it also provides a greater efficiency of the active agent retinoid. In this, the inventors surprisingly have found effectiveness of the disclosed formulations as chemical peeling agents. As such, the disclosed retinoid formulations, delivery systems and methods of use thereof function as chemical peels in their own right at a cosmetic strength, as compared with clinical/dermatological strength chemical peel agents, as discussed in more detail hereinafter, without skin irritation typically associated with such formulations.

The antioxidant can be a polyphenol that is isolated from plants, chemically synthesized; the antioxidant can also be a semi-synthetic compound prepared by modification of a natural polyphenol or mixture of polyphenols. In specific embodiments of the present disclosure, the antioxidant includes "green tea polyphenols" isolated and purified from the leaves of *Camellia sinensis* plants. These antioxidants, as formulated and delivered herein, provide antioxidant activity as well as anti-inflammatory activity, and, further, provide skin soothing, protection, anti-irritant, and repair activity. Inventors unexpectedly have found that presence of antioxidants, e.g., polyphenols, in the manner disclosed herein in retinoid formulations of the present disclosure provides better toleration with respect to the retinoid formulations, i.e., reduces and/or eliminates irritation and redness arising from use of the formulations as, e.g., chemical peeling agents and daily use cosmetic products.

The present disclosure provides formulations comprising one or more retinoids, including retinol, that are useful in the disclosed delivery system. The disclosed formulations provide retinoid stability, low irritancy, and efficient release of the active agent retinoid/retinol, when applied to the skin. In one aspect of this disclosure, the skin is human skin. In other aspects of the present disclosure, the skin is that of a companion animal, a domestic animal, or a commercially useful animal.

Inventors believe, without wishing to be held to that belief, that the retinoid agents disclosed herein may be used effectively up to the day of skin treatment, such as chemical peeling, as pre-treatment agents. Inventors further believe, without wishing to be held to that belief, that unexpected results associated with the retinoid/retinol formulations are obtained by the synergistic operation of the delivery systems herein, i.e., the functioning of the delivery systems resulting in control release of the retinoid active agent(s). In this, the disclosed delivery systems and formulations release the active agents at maximum, optimum strength and rate of release without irritation to the skin.

In particular embodiments, formulations and delivery systems of the present disclosure comprise 0.01 to 1.0% retinol. In various aspects of these embodiments, formulations and delivery systems of the present disclosure comprise 0.02 to 1.0% retinol, 0.03% to 1.0% retinol, 0.04 to 1.0% retinol, 0.05 to 1.0% retinol, 0.06 to 1.0% retinol, 0.07 to 1.0% retinol, 0.08 to 1.0% retinol, 0.09% to 1.0% retinol, 0.1% to 1.0% retinol, 0.2% to 1.0% retinol, 0.3% to 1.0% retinol, 0.4% to 1.0%, or 0.5% to 1.0% retinol. Such formulations and delivery systems can be, for example, those used in consumer products.

In specific aspects of these embodiments, formulations and delivery systems of the present disclosure comprise 0.1%, 0.2%, 0.3%, 0.5%, 0.75%, or 1.0% retinol In particular embodiments, formulations and delivery systems of the present disclosure, comprise 1.0 to 50.0% retinol. Such formulations and delivery systems can be, for example, those used by physicians in in-office procedures.

Inventors believe, without wishing to be held to that belief, that the increased efficiency of delivery of the active agent retinoid coupled with the marked reduction in irritation observed upon administration of the presently disclosed retinoid formulations and delivery systems, permit the formulation and use of retinoid delivery systems with significantly higher concentrations of retinoid than previously employed. As such, the presently disclosed retinoid formulations and delivery systems provide effective chemical peeling agents at cosmetic strength.

Inventors believe, without wishing to be held to that belief, that the retinoid, retinol, and/or all trans-retinol of the presently disclosed formulations and delivery systems contributes to an increase in skin cell turnover, supports collagen production in the skin, and brightens areas of hyperpigmentation of the skin. As such, inventors further believe, without wishing to be held to that belief, that such beneficial skin activity is a consequence of different genes that are switched on by the retinoid/retinol formulations disclosed herein.

Inventors similarly believe that, as formulated and delivered herein, the pure and active form of vitamin A, i.e., all trans-retinol, provides effective topical treatment with a low incidence of irritation, supports the skin barrier, and as noted increases cell turnover in the skin, thereby reducing the appearance of fine lines, wrinkles, and age spots, as well as improving skin texture and tone and promoting a collagen-rich appearance. As used herein, "pure" refers to potency or activity measured as the percentage content of the referenced component or agent.

Antioxidants, particularly the green-tea polyphenols, as well as retinol, are generally recognized as notoriously difficult to stabilize, as both are subject to oxidation and/or degradation by oxygen, moisture, light, trace metals, as well as other ingredients frequently included in formulations. This is particularly apparent with respect to topical formulations that present a large surface area when spread on the skin, thereby facilitating air-oxidation of susceptible components of the applied formulation and/or when seeking a stable long term shelf life of the formulations, for example, 2 years. Surprisingly and unexpectedly, the disclosed formulations and delivery systems overcome these issues, providing unique, stable, non-irritating, and efficacious systems for topical application to the skin.

The disclosed delivery system comprises one or more polymers acting as, inter alia, solvents. In one aspect of this embodiment, the polymer is a silicone elastomer. In another aspect, the silicone elastomer exhibits a degree of polarity, provided, for example, by ethoxylation or propoxylation or by modification with other materials that provide a degree of polarity to the silicone elastomer. In one specific aspect of this embodiment, the polymer is a PEG-12 dimethicone/PPG-20 copolymer.

The disclosed delivery system also comprises one or more solubilizing agents and/or emulsifiers and/or dispersants. In one aspect of this embodiment, the solubilizing agent/emulsifier/dispersant is a non-ionic solubilizing agent/emulsifier/dispersant. In one specific aspect of this embodiment, the solubilizing agent/emulsifier/dispersant is caprylyl methicone. In another specific aspect of this embodiment, the solubilizing agent/emulsifier/dispersant is PEG/PPG-18/18 dimethicone. In still another specific aspect of this embodiment, the solubilizing agent/emulsifier/dispersant is polysorbate 20. Polysorbate 20 also provides stability to the disclosed formulations and retinoid delivery systems. In another specific aspect of this embodiment, the solubilizing agent/emulsifier/dispersant is mixture of two or more materials including, but not limited to a mixture two or more of caprylyl methicone, PEG/PPG-18/18 dimethicone, and polysorbate 20.

The disclosed delivery system also comprises at least one retinoid source. In one aspect of this embodiment, the retinoid may be retinol, retinoic acid, retinaldehyde, an ester of retinol or of retinoic acid, including, e.g., palmitate, acetate, propionate, butyrate, hexanoate, heptanoate, caprylate, and stearate esters of retinol or retinoic acid, or a synthetic retinoid such as, but not limited to, adapalene, bexarotene, tazarotene, or a combination of two or more thereof. The retinoid or retinol is an oily substance that is solubilized by the formulations disclosed herein. In one aspect of this embodiment, the retinoid is retinol. In another aspect the retinoid is all trans-retinol.

The disclosed delivery system also comprises at least one liquid carrier/diluent. In one aspect of this embodiment, the liquid carrier/diluent is a silicone. In another aspect of this embodiment, the silicone is mixed with or contains a volatile component. In one specific aspect, the carrier/diluent is dimethicone; in another specific aspect the carrier/diluent is cyclomethicone. In a further aspect, the carrier/diluent is a mixture comprising dimethicone and cyclomethicone. In yet a further aspect, the carrier/diluent is caprylyl methicone.

The disclosed delivery system may also comprise one or more antioxidants. In one aspect of this embodiment, the antioxidant is a polyphenol. In a more specific aspect of this embodiment, the antioxidant comprises a polyphenol isolate of *Camellia sinensis*. In a further aspect, the anti-oxidant is 90% polyphenol isolate of *Camellia sinensis*.

The disclosed delivery source may also comprise a xanthine related compound, polymeric derivative thereof, or mixture of xanthine-related materials that can function as antioxidants or stimulators of antioxidant activity. In one specific aspect, the xanthine-related compound is caffeine. In another specific aspect, caffeine of the disclosed formulations and delivery systems is pure, very pure, or USP grade caffeine.

The disclosed delivery system may also comprise one or more moisturizers and/or humectants. In one aspect of this embodiment, the moisturizer and/or humectant is sodium hyaluronate. Hyaluronate is a moisture binder that helps keep the skin hydrated and provides "slip" (sensory aesthetics) to the disclosed formulations.

The disclosed delivery system may also comprise one or more emollients. In one aspect of this embodiment, the emollient may be an ester, oil, or silicone. In various aspects of this embodiment, the emollient can include one or more of the following shea butter, cocoa butter, mineral oil, lanolin, petrolatum, paraffin, beeswax, squalene, cetyl alcohol, olive oil, triethylhexanoin, coconut oil, jojoba oil, sesame oil, almond oil, or other plant oils, omega-6 fatty acids, licochalcone, primrose oil, grape seed oil, ceramide, and combinations of two or more thereof.

In representative embodiments, formulations and delivery systems of the present disclosure comprise caprylyl methicone, PEG-12 dimethicone/PEG-20 crosspolymer, dimethicone, caffeine, cyclomethicone, PEG/PPG-18/18 dimethicone, *Camellia sinensis* (Green Tea) polyphenols, retinol, sodium hyaluronate, and polysorbate 20.

In such formulations, caprylyl methicone, PEG-12 dimethicone/PPG-20 crosspolymer, PEG/PPG-18/18 dimethicone, and polysorbate 20 are principally responsible for carrying and delivering the co-formulated retinol. In some embodiments, dimethicone serves as an occlusive to aid in retinol penetration, and the green tea polyphenols reduce the potential for irritation. The PEG/PPG-18/18 dimethicone is an emulsifying silicone.

In particular embodiments of the present disclosure, caprylyl methicone and PEG-12 dimethicone/PPG-20 are added as a mixture; additional caprylyl methicone can be included in and added to the formulations disclosed in order to disperse and/or solubilize other components of the formulation.

In particular embodiments of the present disclosure, the formulated dimethicone, i.e., polydimethylsilane, has a viscosity (centipoise; cps) within the range of 1 cps to 1000 cps.

Cyclomethicones of various ring sizes (measured by the number of siloxane units in the ring) can be used in the formulations disclosed herein. These include, for example cyclopentasiloxane (D5) and cyclohexasiloxane (D6). In particular aspects of the present disclosure, the cyclomethicone is D6, cyclohexasiloxane.

The antioxidant included in the disclosed retinoid formulations and delivery systems may include *Camellia sinensis* (green tea) polyphenols. In particular embodiments, a purified isolate of *Camellia sinensis* (green tea) polyphenols is included in the formulations. The present disclosure contemplates that the purity of the polyphenols may range from trace amounts obtained, for example, from green tea extracts to 100% pure polyphenols. Although, in various embodiments, any *Camellia sinensis* (green tea) preparation of polyphenols may be formulated, in specific aspects of this embodiment, a 90% or 95% purified preparation of *Camellia sinensis* (green tea) polyphenols is formulated. In various other formulations, the amount of polyphenol antioxidant added is inversely related to the purity thereof.

The antioxidant included in the disclosed retinoid formulations and delivery systems may include *Camellia sinensis* (green tea) polyphenols which may be a mixture of polyphenol species. In specific aspects, the major component of the formulated polyphenol antioxidant is epigallocatechin gallate (EGCG).

The present inventors have noted that green tea polyphenols in the formulations provide not only potent antioxidant reduction of reactive oxygen species (ROS) but they also provided, very surprisingly, a reduction in the irritation normally associated with retinol use. This observed reduction in the irritation was dramatically better than other antioxidants and anti-irritants. Inclusion of these materials in the disclosed formulations boosts patient compliance. As documented in the trials presented below, patients stay on the treatment regimen because they are not irritated. Thus, although irritation is a major problem with topical retinol applications, it was not observed upon testing with the presently disclosed retinoid delivery systems. In particular, study participants did not drop out of a clinical study even though at least 10-15% of the participants would have been predicted to drop out due to irritation, dryness, itching/burning or retinoid dermatitis based upon historical studies even with much lower levels of formulated retinol. In fact, participants in the studies noted below all indicated that the administered formulations of the present disclosure made their skin feel smoother. Inventors believe, without wishing to be held to that belief, that these effects are in part due to the formulated green tea polyphenols, alone or in combination with the other components of the formulation.

Inventors believe, without wishing to be held to that belief, that the antioxidant component of the disclosed formulations and delivery systems, particularly the formulated, therapeutic levels of green tea polyphenols interact synergistically with the formulated retinoid, specifically the all trans-retinol, to build up the skin matrix and alleviate, ameliorate, or eliminate the appearance of UV damage to the skin. Inventors similarly believe that the green tea polyphenols soothe and calm the skin, reducing irritation and that the xanthine, e.g., caffeine, further helps to reduce, alleviate, ameliorate, or eliminate the appearance of redness and irritation of the skin to which the retinoid-containing formulations and retinoid delivery systems have been applied.

Inventors also believe, without wishing to be held to that belief, that the delivery system disclosed herein works differently from other topical treatments, providing a "micro polymer" delivery system capable of delivering essentially all, up to 100%, of the formulated retinoid or retinol into the skin. The disclosed formulations effectively trap the retinoid, e.g. retinol and/or all trans-retinol, prevent oxidation thereof while applied to the skin, and provide a continuous, time-released delivery, thereby establishing a reservoir of protected, stabilized retinol that continuously bathes the skin. The disclosed retinoid formulations and delivery systems shield the formulated retinoid, e.g. retinol and/or all trans-retinol, from oxidation while applied to the skin.

In one embodiment of the present disclosure, the retinoid containing formulation includes the following components: caprylyl methicone, PEG-12 dimethicone/PPG-20 crosspolymer, dimethicone, caffeine, cyclomethicone, PEG/PPG-18/18 dimethicone, *Camellia sinensis* green tea polyphenols, retinol, sodium hyaluronate, and polysorbate 20. The *Camellia sinensis* green tea polyphenol is, preferably, used as a 90%-95% pure preparation and the retinol is, preferably, all trans-retinol, and more preferably the retinol is preferably at least 90% pure all trans-retinol, and even more preferably, the retinol is preferably at least 95% pure all trans-retinol, which may be sourced pre-dispersed in a vehicle or as a solution.

In other embodiments of the present disclosure, the retinoid containing formulation includes the following components formulated within the indicated ranges (all expressed as % w/w): caprylyl methicone (5%-85%), PEG-12 dimethicone/PPG-20 crosspolymer (5%-20%), dimethicone (0.01%-40%), caffeine (0.01%-10%), cyclomethicone (0.01%-40%), PEG/PPG-18/18 dimethicone (0.1%-10%), *Camellia sinensis* green tea polyphenols (0.1%-25%), retinal (0.001%-60%), sodium hyaluronate (0.01%-5%), and polysorbate 20 (0.01%-25%). The *Camellia sinensis* green tea polyphenol is, preferably, used as a 90%-95% pure preparation and the retinol is preferably all trans-retinol, and more preferably, the retinol is preferably at least 90% pure all trans-retinol, and even more preferably, the retinol is preferably at least 95% pure all trans-retinal, neat, e.g., undiluted, or in a suitable vehicle.

In certain embodiments of the present disclosure, the retinoid containing formulation includes the following components formulated within the indicated ranges (all expressed as % w/w): caprylyl methicone (40%-70%), PEG-12 dimethicone/PPG-20 crosspolymer (10%-20%), dimethicone (10%-20%), caffeine (1%-5%), cyclomethicone (0.1%-3%), PEG/PPG-18/18 dimethicone (1.0%-2.5%), *Camellia sinensis* green tea polyphenols (1.0%-5%), retinol (0.1%-1.0%), sodium hyaluronate (0.01%-1%), and polysorbate 20 (0.1%-5%). The *Camellia sinensis* green tea polyphenols is, preferably, used as a 90%-95% pure preparation and the retinol is, preferably, all trans-retinol, and more preferably the retinol is preferably at least 90% pure all trans-retinol, and even more preferably, the retinol is preferably at least 95% pure all trans-retinol, obtained neat or in a suitable vehicle.

In further embodiments, the all trans-retinol of the above described formulations can be substituted with or supplemented by one or more of the following retinoids at the indicated percentage by weight (% w/w) levels: retinaldehyde (0.01%-1%), esters of retinol (0.01-5%), retinoic acid (0.01%-0.2%), synthetic retinoids, e.g., adapalene (0.02-0.5%), tazarotene (0.01%-0.2%).

In still further embodiments, the all trans-retinol of the above described formulations can be substituted with or supplemented by one or more of the following retinoids at the indicated (% w/w) levels: retinaldehyde (0.05-0.10%), esters of retinol (0.1-2%), retinoic acid (0.02%-0.15%), synthetic retinoids, e.g., adapalene (0.1-0.3%), tazarotene (0.05%-0.1%).

In certain embodiments, the dosage of the formulation or delivery system of the present disclosure to be applied to the skin is within the range of from 0.01 g to 5 g, from 0.02 g to 4 g, from 0.05 g to 3 g, from 0.1 g to 2 g, from 0.2 g to 1 g. In one aspect of these embodiments, the dosage of the formulation or delivery system of the present disclosure to be applied to the skin can be 0.4 g. The actual dosage applied will depend on, inter alia, the condition to be treated, the particular regimen to be followed, and the personal preferences of the user. For example, different dosages may be used for spot treatment, multi-spot treatment, full or partial face treatment, treatment of parts of the body, such as neck, hands, among others.

Formulations and delivery systems of the present disclosure may be prepared under ambient conditions. In certain embodiments, formulations and delivery systems of the present disclosure are prepared under an inert atmosphere. In particular aspect of this embodiment, the inert atmosphere is an inert gas, such as but not limited to, nitrogen, argon, or combinations thereof. In certain embodiments, formulations and delivery systems of the present disclosure are prepared under a dry inert atmosphere, which may comprise, consist essentially of, or consist of one or more dry inert gases, including but not limited to dry nitrogen, dry argon, or a combination thereof.

EXAMPLE

The following study was carried out with 10 human female subjects of 35 to 60 years of age. All considered themselves not only to be free of disease and infirmity but also to be in generally good physical and mental health and to possess good social well-being.

Each of the subject possessed a Fitzpatrick skin type of Type I to Type IV, where, e.g., in response to ultraviolet light, Type I skin "always burns"; Type II "usually burns"; Type III "sometimes (mildly) burns"; and Type IV "burns minimally."

The subjects exhibited mild to moderate eye area wrinkles ("crow's feet" or under eye wrinkles), mild to moderate global facial hyperpigmentation, and mild to moderate global facial visible laxity, i.e., scores of 3-6 on each parameter according to a modified Griffiths' scale, where 0=none and 9=severe (see, e.g., Griffiths et al., "A Photonumeric Scale for the Assessment of Cutaneous Photodamage," *Arch Dermatol.* 1992; 128(3):347-351).

Subjects applied aliquots of a presently-disclosed topical formulation to clean skin once a day in the evening. After six weeks of treatment, in response to a questionnaire, 83% of patients agreed that their skin showed an improvement in skin tone evenness, 92% of patients agreed that their skin had an improvement in fine lines, and 100% of patients agreed that their skin had an improved facial clarity/radiance.

The data obtained demonstrate the effectiveness of the disclosed topical retinoid containing formulations and delivery systems for improvement in skin properties.

What is claimed is:

1. A topical formulation comprising a silicone elastomer, a solubilizing agent, a retinoid, and a silicone based liquid carrier, and
   wherein the silicone elastomer is PEG-12/PPG-20 crosspolymer and is included in an amount of 10%-20%.

2. The formulation of claim 1, further comprising one or more of an antioxidant, a xanthine, a moisturizer, and an emollient.

3. The formulation of claim 1, wherein the retinoid is all trans-retinol.

4. The formulation of claim 1, wherein the solubilizing agent is at least one of caprylyl methicone, PEG/PPG-18/18 dimethicone, polysorbate 20, and mixtures thereof.

5. The formulation of claim 1, wherein the silicone based liquid carrier is at least one of dimethicone, cyclomethicone, and mixtures thereof.

6. The formulation of claim 2, wherein the antioxidant is *Camellia sinensis* polyphenols.

7. The formulation of claim 2, wherein the xanthine is caffeine.

8. The formulation of claim 2, wherein the moisturizer is sodium hyaluronate.

9. The retinoid formulation of claim 1 comprising (% w/w) at least one of:
   5%-85% caprylyl methicone;
   0.1%-40% dimethicone;
   0.1%-10% caffeine;
   0.01%-40% cyclomethicone;
   0.1%-10% PEG/PPG-18/18 dimethicone;
   0.1%-2.5% *Camellia sinensis* green tea polyphenols;
   0.001%-60% retinol;
   0.001%-5% sodium hyaluronate; and
   0.01%- 25% polysorbate 20.

10. The formulation of claim 9, wherein the *Camellia sinensis* green tea polyphenols is a 90%-100% pure preparation and wherein the retinol is all trans-retinol.

11. The formulation of claim 10, wherein the all trans-retinol is at least 90% pure all trans-retinol, either neat or in a vehicle.

12. The formulation of claim 11, wherein the all trans-retinol is at least 95% pure all trans-retinol, either neat or in a vehicle.

13. The formulation of claim 1, comprising (% w/w) at least one of:
   40%-70% caprylyl methicone;
   10%-20% dimethicone;
   1%-5% caffeine;
   0.1%-3% cyclomethicone,
   1.0%-2.5% PEG/PPG-18/18 dimethicone;
   1.0%-5% *Camellia sinensis* green tea polyphenols;
   0.1%-1.0% retinol;
   0.01%-1.0% sodium hyaluronate;
   0.1%-5% polysorbate 20.

14. The formulation of claim 13, wherein the *Camellia sinensis* green tea polyphenols is a 90% to 100% pure preparation and wherein the retinol is all trans-retinol.

15. The formulation of claim 14, wherein the all trans-retinol is at least 90% pure all trans-retinol, either neat or in a vehicle.

16. The formulation of claim 15, wherein the all trans-retinol is at least 95% pure all trans-retinol, either neat or in a vehicle.

17. A method for therapeutic treatment of a dermatological condition, comprising topically applying to an affected area a therapeutically effective amount of a formulation comprising a silicone elastomer, a solubilizing agent, a retinoid, and a silicone based liquid carrier, wherein the silicone elastomer is PEG-12/PPG-20 crosspolymer and is included in an amount of 10%- 20%, and the therapeutic treatment includes exfoliating the skin.

18. The method of claim 17, wherein the affected area is one or more of human skin, scalp, hair, nails.

19. The method of claim 17, wherein the retinoid is retinol.

20. The method of claim 17, wherein the retinoid is all trans-retinol.

21. The method of claim 17, wherein the formulation further comprises one or more of an antioxidant, a xanthine, a moisturizer, and an emollient.

22. The method of claim 17, wherein applying the formulation includes peeling the skin by applying the formulation.

23. The method of claim 17, wherein exfoliating affected skin comprises chemical peeling of the affected skin.

24. The formulation of claim 1, wherein a dosage of the formulation to be applied to skin is from 0.01 g to 5 g.

* * * * *